(12) United States Patent
Teske (10) Patent No.: US 8,519,280 B2
(45) Date of Patent: Aug. 27, 2013

(54) ELECTRICAL FEEDTHROUGH, METHOD FOR THE PRODUCTION AND USE THEREOF

(75) Inventor: Josef Teske, Hallstadt (DE)

(73) Assignee: Biotronik SE & Co. KG, Berlin (DE)

( * ) Notice: Subject to any disclaimer, the term of this patent is extended or adjusted under 35 U.S.C. 154(b) by 267 days.

(21) Appl. No.: 13/043,927

(22) Filed: Mar. 9, 2011

(65) Prior Publication Data
US 2011/0232962 A1 Sep. 29, 2011

Related U.S. Application Data

(60) Provisional application No. 61/318,407, filed on Mar. 29, 2010.

(51) Int. Cl.
*H02G 3/18* (2006.01)

(52) U.S. Cl.
USPC ............... 174/650; 174/152 GM; 174/50.51; 361/302; 361/306.1; 607/36

(58) Field of Classification Search
USPC .............. 174/650, 152 GM, 520, 50.5, 50.51, 174/50.52; 429/181; 361/302, 307, 306.1; 333/182; 607/36, 37
See application file for complete search history.

(56) References Cited

U.S. PATENT DOCUMENTS

| | | | | |
|---|---|---|---|---|
| 4,292,464 | A | * | 9/1981 | Vogt et al. ............. 174/152 GM |
| 5,104,755 | A | * | 4/1992 | Taylor et al. ................ 174/50.61 |
| 5,406,444 | A | * | 4/1995 | Selfried et al. ................ 361/302 |
| 6,031,710 | A | * | 2/2000 | Wolf et al. ............ 174/152 GM |
| 6,274,252 | B1 | * | 8/2001 | Naugler et al. ........ 174/152 GM |
| 6,903,268 | B2 | * | 6/2005 | Marshall et al. ....... 174/152 GM |
| 7,966,070 | B2 | * | 6/2011 | Taylor et al. .................... 607/36 |
| 8,288,654 | B2 | * | 10/2012 | Taylor et al. .......... 174/152 GM |

* cited by examiner

*Primary Examiner* — Angel R Estrada
(74) *Attorney, Agent, or Firm* — Buchanan Ingersoll & Rooney PC (57) ABSTRACT

A feedthrough, in particular for use in a medical-electronic implant, is provided having a terminal pin which has a section which can be soft soldered at least in the interior of the implant, a flange enclosing the terminal pin, and a glass solder plug which hermetically seals the terminal pin in relation to the flange.

20 Claims, 10 Drawing Sheets

ELECTRICAL FEEDTHROUGH, METHOD FOR THE PRODUCTION AND USE THEREOF

RELATED APPLICATION

This patent application claims the benefit of U.S. Provisional Patent Application No. 61/318,407, filed on Mar. 29, 2010, which is hereby incorporated by reference in its entirety.

TECHNICAL FIELD

The present invention relates to a so-called electrical feedthrough (the terminal pin area) and, additionally, to a method for the production and use thereof.

BACKGROUND

Electrical feedthroughs have been known for some time in the implantology of electrical implants. They are used for the purpose of leading electrical contacts outward from the interior of the implant insulated from the implant housing, without the tightness of the implant being endangered.

In a simple construction, a feedthrough includes an electrically conductive flange, which includes the same material as the implant housing (typically titanium), and a terminal pin, with the aid of which the electrical contact is produced between the implant interior and its surroundings. The terminal pin is led inside an insulator, which preferably consists of a ceramic or solely of a glass solder, which is in turn connected on its outer side to the flange. Such electrical feedthroughs are typically implemented as round and usually lead one, or normally also multiple, terminal pin(s) (also referred to as multiple feedthroughs). However, single feedthroughs which have a common flange are also suitable.

Problems may occur if the terminal pins are joined, on the side lying in the implant interior, to an electrical circuit using thermal methods, for example. In this case, heat damage may occur on the electrical circuit located in the implant, for example, if the terminal pin can only be joined using brazing or welding methods. Therefore, the terminal pin is to include a material which can be soft soldered easily, i.e., can also be wetted easily using soft solder, so that the circuit is not damaged during the joining, for example, using reflow soldering. For example, nickel or nickel alloys are known as materials which can be soft soldered. Difficulties arise in the described terminal pins including the described materials which can be soft soldered upon connection of the insulator, because detachment of the insulator can occur and/or the wetting capability with solder is poor. A terminal pin made of niobium (Nb), Pt, Pt/Ir, FeNi, FeNiCo, FeCr, Ta, Mo, W, Cr, FeCr, V, Ti, and further metals or their alloys, for example, may advantageously be hermetically connected to the insulator as well, but niobium can only be welded and is therefore not usable for being electrically connected to an electrical circuit.

The present invention is directed at overcoming one or more of the above-mentioned problems.

SUMMARY

The present invention is therefore based on the object of improving the construction of an electrical feedthrough so that, on the one hand, it can be soft soldered, and, on the other hand, it allows an optimum and permanent secure hermetic seal.

This object is achieved according to its device aspect by a feedthrough having the features of the apparatus claims and, according, to relatively independent method aspects by a method having the features of the method claims. Expedient refinements of the idea of the invention are the subject matter of the dependent claims.

The present invention includes the essential idea of implementing the feedthrough according to the species as hermetically sealed, the feedthrough separating the capacitor interior in relation to the capacitor exterior hermetically sealed from one another. Furthermore, it includes the idea of providing a glass solder plug which hermetically seals the terminal pin in relation to the flange. The terminal pin is implemented so it can be soft soldered at least on a section lying in the interior of the implant for this purpose. In connection with the present invention, it is significant that exclusively terminal pin surfaces which can be soft soldered are provided in the interior of the implant.

An expedient embodiment of the present invention provides that the terminal pin, in the area of its length in which it is in contact with the glass solder plug, has at least one core made of a material which has approximately the same or a lesser coefficient of thermal expansion as the glass solder. In this way, greater impermissibly high mechanical tension strains in the glass solder may be fundamentally avoided during the production and the use of the finished feedthrough. The material of the terminal pin or its core, in the area of its length in which it is in contact with the glass solder plug, can especially include Pt, Pt/Ir, FeNi, FeNiCo, FeCr, Nb, Ta, Mo, W, Cr, FeCr, V, Ti, and further metals or their alloys.

Furthermore, it is provided that the section of the terminal pin which can be soft soldered in the interior of the implant is a nickel pin. For expedient processing with the glass solder in the sealing section of the feedthrough, a design is advisable in which a pin made of Pt, Pt/Ir, FeNi, FeNiCo, FeCr, Nb, Ta, Mo, W, Cr, FeCr, V, Ti, and further metals or their alloys, is joined, in particular soldered, welded, crimped or glued in an electrically conductive manner onto the nickel pin via a joint. To make the further process control easier, in particular the interior nickel pin can have a nailhead, which can be flattened, curved, provided with an attached bush or disk, or formed in another way. This makes subsequent soft soldering of the inner terminal easier, especially also using a reflow method.

A further preferred construction of the proposed feedthrough is distinguished in that the terminal pin is enclosed in the flange by a ceramic ring, in particular made of Al2O3 ceramic, so that the ceramic ring forms a terminus for the glass solder plug during the soldering process and thus positively influences the glass shape so that the glass solder plug can achieve a hermetic seal during the production of the feedthrough at a higher yield. Such a combined glass-ceramic feedthrough additionally obtains high mechanical stability through the high-quality rigid ceramic components, and a high-quality and reliable electrical insulation section to the adjacent surfaces of the flange and terminal pin is also implemented by the ceramic components. In particular, it offers the glass solder plug mechanical protection in relation to lateral force actions (e.g., bending forces), which may engage on the terminal pin.

Instead of the ceramic ring, one or more capacitor plate(s) can also be provided, in order to thus implement the electrical feedthrough as filtered against electromagnetic influences. The capacitor plate can include multiple plates made of conductive material lying one on top of another, which are separated by dielectric layers. The plates are alternately electrically connected to the flange and the terminal pin, and thus form a filter together with the dielectric layers.

A further preferred construction of the proposed feedthrough is distinguished in that the terminal pin is enclosed in the flange by two ceramic rings, in particular made of Al2O3 ceramic. These two terminal rings enclose the glass plug both on the interior and also on the exterior in the space between the terminal pin and the hole of the aluminum flange and prevent the glass solder plug from running out of the hole area of the flange during the soldering process, so that during the production process a hermetically sealed, mechanically stable, electrically insulating, dimensionally accurate, compact electrical feedthrough having long-term stability can be generated at a higher yield.

In a further embodiment of the present invention, a filler which encloses the terminal pin, or a coating, is provided on the side of the glass solder plug facing toward the inner side of the housing. The filler or the coating is especially dimensioned and situated so that it masks a joint in the terminal pin. This filler or the coating secures the joint from damage or oxidation and thus ensures the reliable function of the electrical feedthrough. The filler can also be provided as a plug, or also as a covering, coating, vapor-deposited coating, inter alia, and is to cover all surfaces of the electrical feedthrough pointing in the direction of the implant interior.

An expedient method control for the production of the feedthrough, which especially allows the use of terminal pin materials having a coefficient of thermal expansion significantly different from the glass solder, is distinguished in that the terminal pin is cooled using a heat sink during the generation of the glass solder plug. Because the terminal pin remains cooler than the glass in this case, the otherwise occurring thermal strains tensions may be controlled enough so that hermetically sealed soldering is achieved. The heat introduction into the glass solder can be performed by, for example, infrared radiation (for example, of a CO2 laser) or inductive heat coupling via the surrounding flange, inter alia.

Moreover, it is advantageous under this aspect to keep the quantity of glass solder low and to keep the effective sealing interface between glass solder and terminal pin small, in order to keep the absolute values of the mechanical strains low between the glass solder plug and pin, because of mutual large differences in the coefficients of thermal expansion.

DESCRIPTION OF THE DRAWINGS

Advantages and expedient features of the present invention also result from the following description of exemplary embodiments and aspects of the embodiments on the basis of the figures. In the figures.

DETAILED DESCRIPTION

Figure 1:
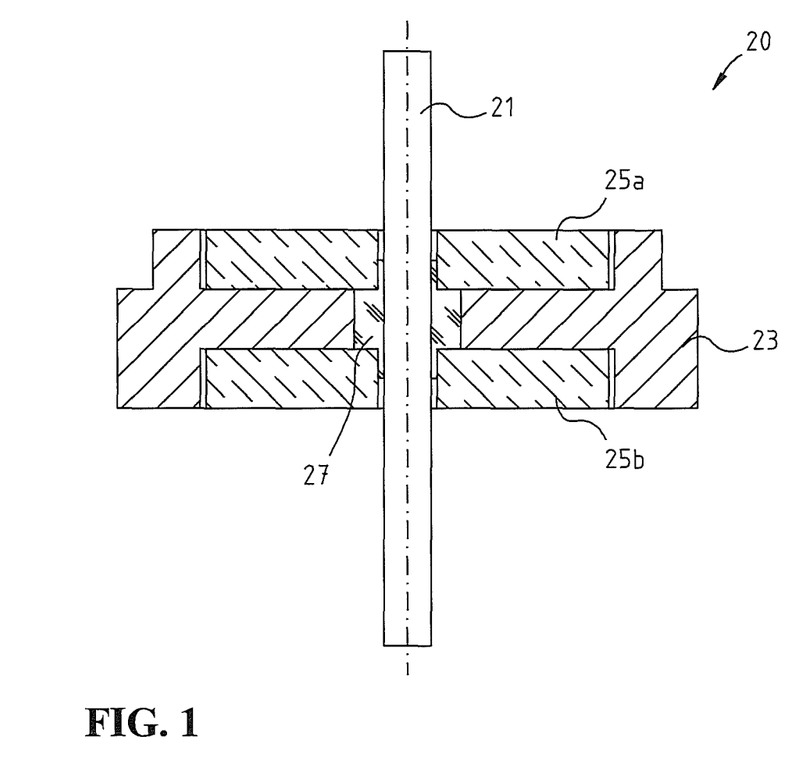
FIGS. 1-3 show longitudinal sectional illustrations of feedthroughs according to embodiments of the present invention.

FIG. 1 shows, as an embodiment of the present invention, a feedthrough 20 having a terminal pin 21, a flange 23 provided on the top and bottom sides with flat cylindrical recesses, and ceramic discs 25a, 25b, each lying in the flange 23, and having a central opening for the passage of the pin 21. A housing wall (not shown here) adjoins the construction on the exterior of the flange 23, and a glass solder plug 27, which hermetically seals both the pin 21 and also the flange 23 against the surrounding surfaces, is located between the central part of the aluminum flange 23 and the inner walls of the central openings of the ceramic discs 25a, 25b and the external surface of the pin 21, so that overall a hermetic seal results between the implant interior and exterior, which is additionally mechanically stable, electrically insulating, dimensionally accurate, geometrically compact, and has long-term stability at a high yield.

A low-melting-point glass solder having a melting temperature significantly below that of the flange material (660° C.) is to be used as the glass solder, for example, a lead-containing solder of the type G 017-052 from Schott having a soldering temperature of approximately 410° C. or a lead-free solder of the type G 018-249, also from Schott, having a soldering temperature of approximately 500° C. Tensions because of the coefficients of thermal expansion, which deviate from one another, of the terminal pin and flange, on the one hand, and the glass solder, on the other hand, may be extensively avoided by the special constructive design, which includes the use of a very small quantity of glass to generate the glass solder plug 27. Furthermore, cooling of the pin 21 via a heat sink is to be viewed as advisable in this meaning.

Figure 2:
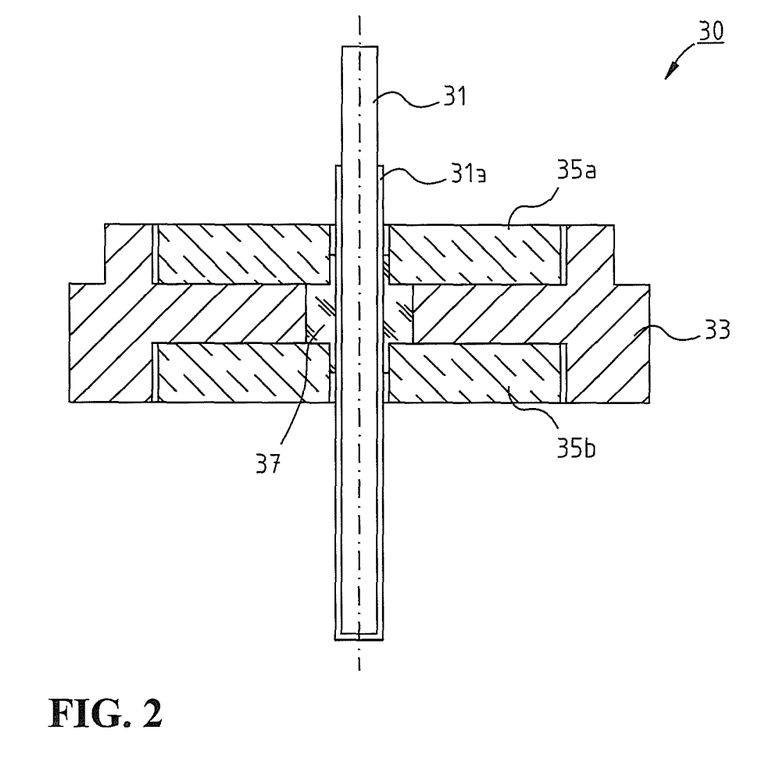

FIG. 2 shows a construction of a further feedthrough 30 which is fundamentally similar to the embodiment according to FIG. 1. Identical or similar parts are identified using reference numerals based on FIG. 2, but in the thirty series of numbers, and are not explained once again here. The essential difference from the embodiment according to FIG. 1 includes the use of a pin 31 made of platinum (Pt), Pt/Ir, FeNi, FeNiCo, FeCr, Nb, Ta, Mo, W, Cr, FeCr, V, Ti, or further metals or their alloys. This pin is provided with a pin section pointing in the direction of the implant interior and the nickel coating 31a, which covers the section located inside the flange 33 and the ceramic discs 35a and 35b. Using this construction of the terminal pin 31, it is adapted better to the coefficient of thermal expansion of the glass, on the one hand, and the attachment of the terminal pin 31 to the electrical circuit is possible through soft soldering and thus using gentle heat, on the other hand.

Figure 3:
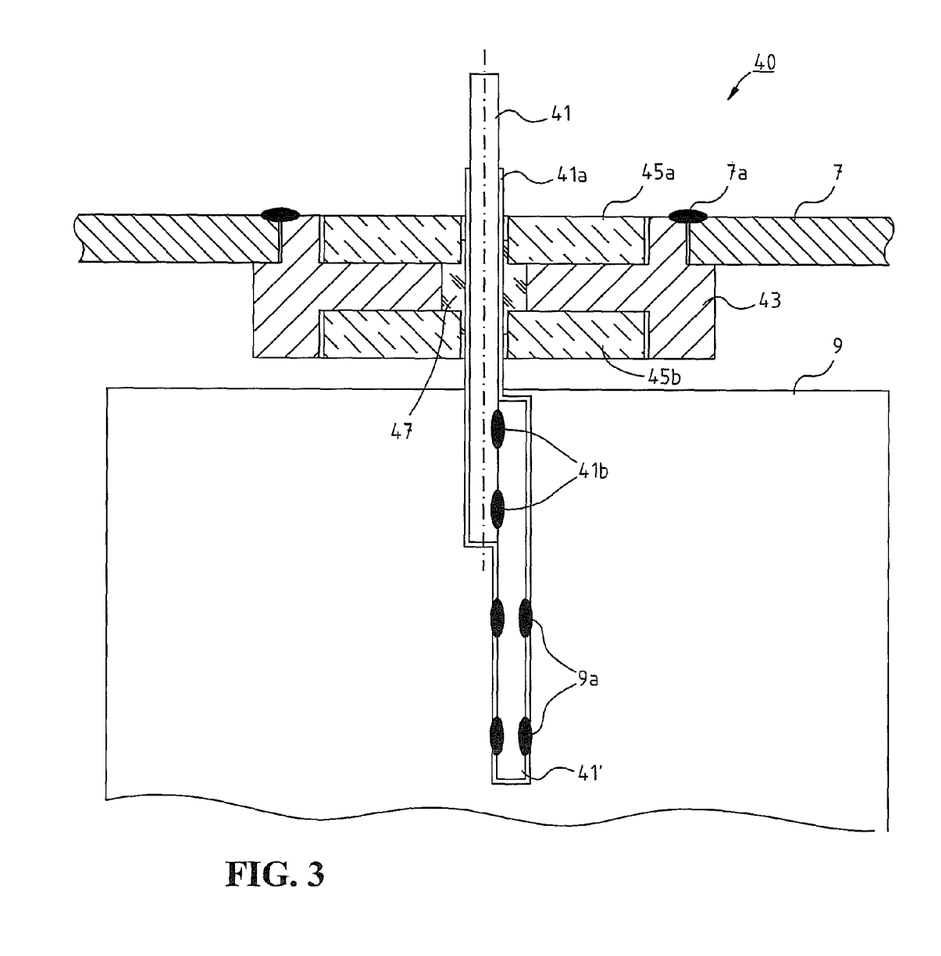

FIG. 3 shows a further feedthrough 40 as a refinement of the embodiment shown in FIG. 2, reference numerals based on FIGS. 1 and/or 2 again being used, but in the forty series of numbers. In addition to the actual feedthrough, in this illustration, the adjoining sections of the housing 7 are also shown, which are connected gas-tight to the flange 43 via a weld seam 7a. Furthermore, FIG. 3 schematically shows a circuit 9, which is located in the interior of the implant and ensures the essential functions of the implant, such as, for example, measuring body signals, outputting pulses, and optionally wireless transmission of data to a device located externally from the body. The circuit 9 is connected to the terminal pin via joints and/or spot welds 9a, which are also schematically shown.

A further special feature of the construction according to FIG. 3 is that the terminal pin is constructed herein from an external pin 41 made of, for example, Pt, Pt/Ir, FeNi, FeNiCo, FeCr, Nb, Ta, Mo, W, Cr, FeCr, V, Ti, or further metals or their alloys, and an internal pin 41' made of, for example, nickel, which are connected to one another via joints 41b, which are implemented by welding, soldering, crimping, electrically conductive gluing, or another suitable method, for example. It is thus ensured that the circuit can be connected to a material capable of a connection which can be soft soldered and remains permanently connected.

Figure 4:
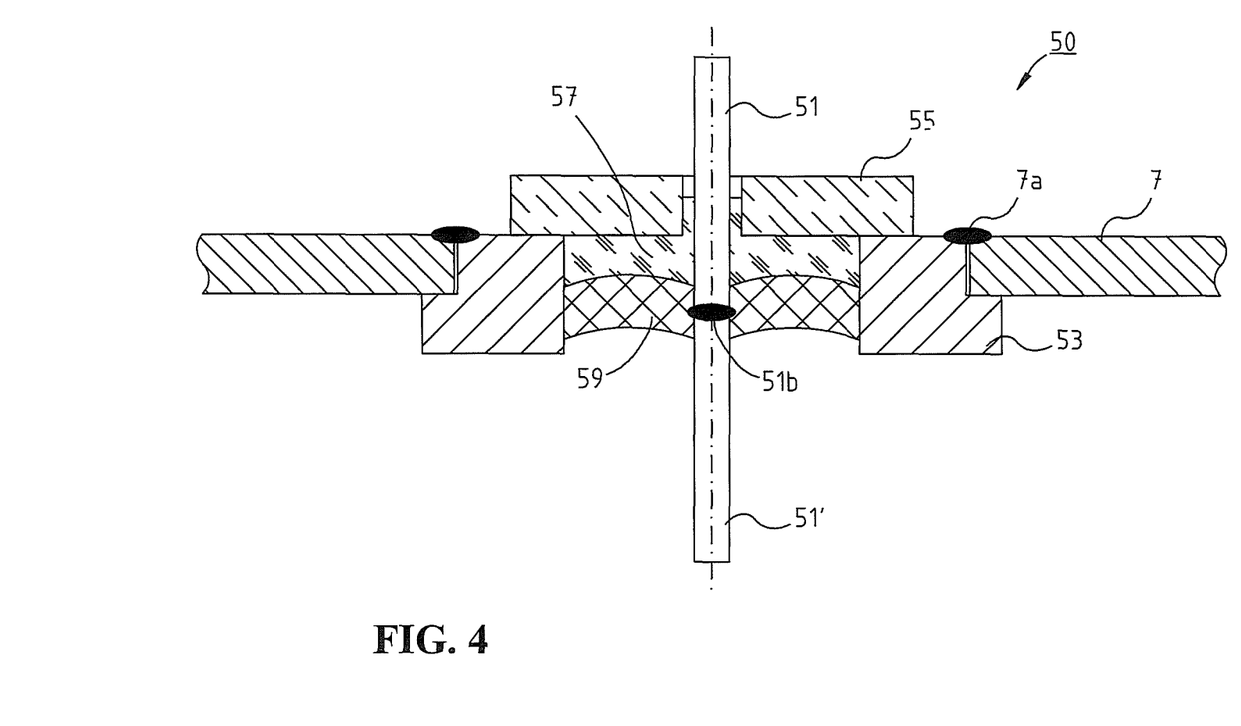
FIGS. 4-8 show longitudinal sectional illustrations of feedthroughs according to further embodiments of the present invention, having additional filler.

FIG. 4 shows a further feedthrough 50 according to the invention having an assembled terminal pin 51/51' made of a first pin section 51 made of, for example, Pt, Pt/Ir, FeNi, FeNiCo, FeCr, Nb, Ta, Mo, W, Cr, FeCr, V, Ti, or further materials or their alloys, or a similar material, and a second pin section 51' made of, for example, nickel. Both sections are connected to one another via a joint 51b, which is implemented by welding, soldering, crimping, electrically conductive gluing, or another suitable method.

Further differences from the preceding embodiments include the provision of a flange 53 having a constructively simpler design and a single ceramic disc 55, which rests flatly on the top side of the flange 53 here. The use of a pin section 51 whose coefficient of thermal expansion is adapted to or less than that of the glass plug 57 has the result that the common sealing length may be greater than in the event of the use of a typical one-piece pin, and the glass may thus be implemented having a greater volume, and a higher mechanical stability of the construction is thus achieved. Its surface facing toward the implant interior and the end of the outer pin section 51 protruding slightly therefrom and the joint 51b are embedded in a filler plug 59. The filler is, for example, rubber, a silicone compound, a polymer, or another halogen-free or chlorine-free plastic. The filler plug 59 ensures that the joint 51b is protected from damage and oxidation and the function of the terminal pin is thus ensured.

Figure 8:
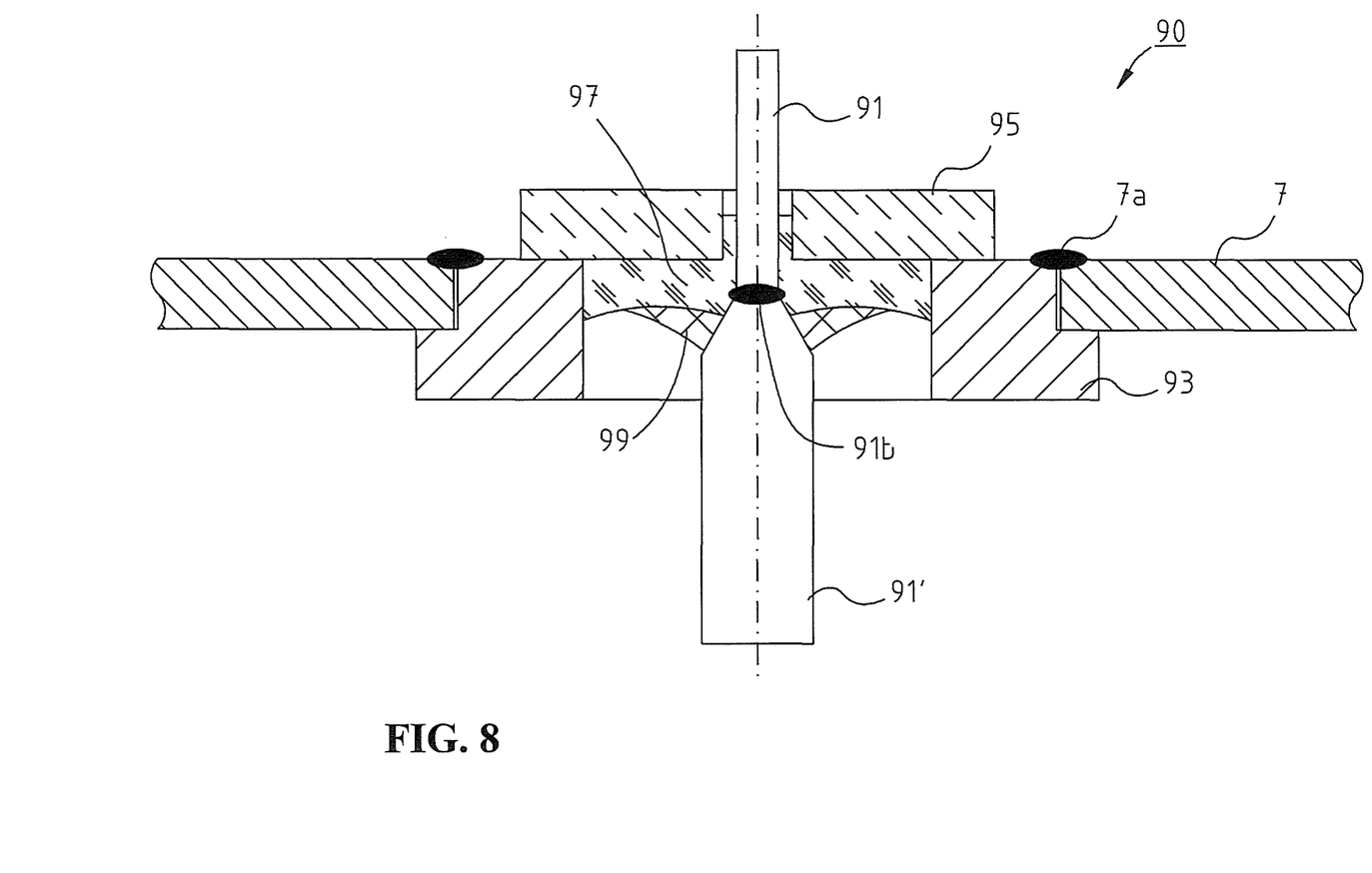

In a design variant of feedthrough 90 shown in FIG. 8, at least the joint 91b and the part of the pin 91' adjoining thereon and the transition to the exposed surface of the glass plug 97 are covered by a filler plug 99. The filler plug 99 can also be implemented as a comparatively thin coating, which saves volume.

Figure 9:
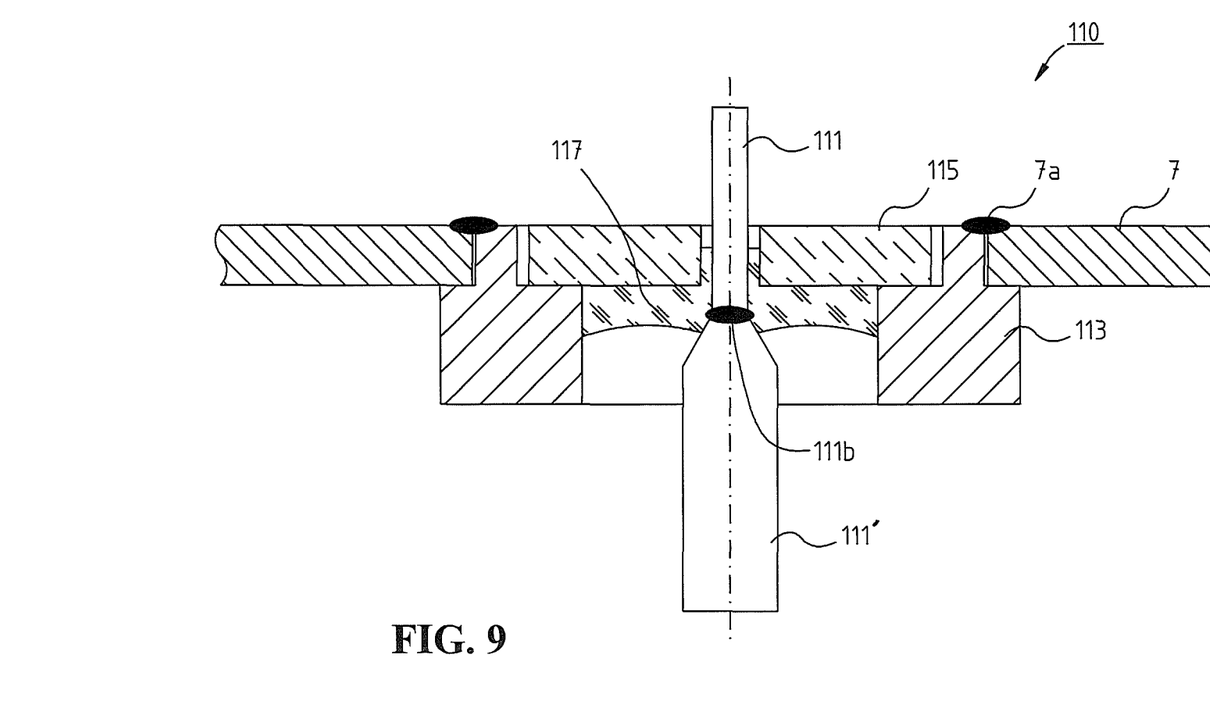
FIGS. 9 and 10 show longitudinal sectional illustrations of feedthroughs according to embodiments of the present invention, having a special terminal pin form.
Figure 10:
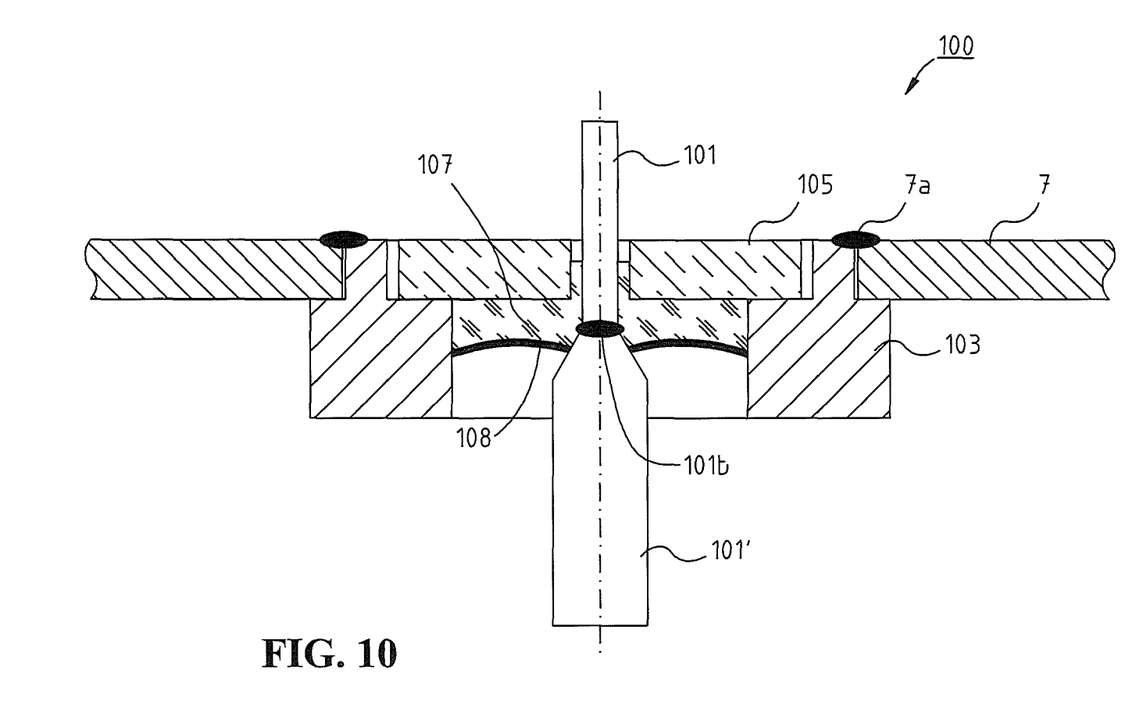

In a further design variant of feedthrough 110 shown in FIG. 9, the joint 111b can be entirely or partially enclosed and, alternatively, additionally a part of the pin section 111' can be enclosed by the glass plug 117. Even in the event of simultaneous enclosure of the joint 111b and the adjoining part of the pin section 111' by the glass plug 117, because of the comparatively large coefficients of thermal expansion of the joint 111b and the pin 111', a hermetically sealed closure of these parts in relation to the implant interior generally cannot be ensured. This task is to be taken over in a feedthrough variant 100 shown in FIG. 10 by a filler plug or by a corresponding coating 108, which at least completely covers the transition from the glass plug 107 to the pin 101' and/or to the joint 101b and thus masks it in relation to the implant interior.

In a further design variant, two ceramic rings enclose the glass plug from the inside and outside, the two-part pin being led through an opening of the ceramic rings and being enclosed hermetically sealed by the glass plug. The joint can be located entirely or partially inside the glass plug and entirely or partially inside the inner ceramic ring located in the implant interior. In a preferred design variant, at least the joint, the pin section, and alternatively additionally also the glass plug are covered by a filler plug and/or a coating. The inner ceramic ring and the flange, as well as the housing, can be entirely or partially covered and/or wetted by the filler plug and/or the coating.

Figure 5:
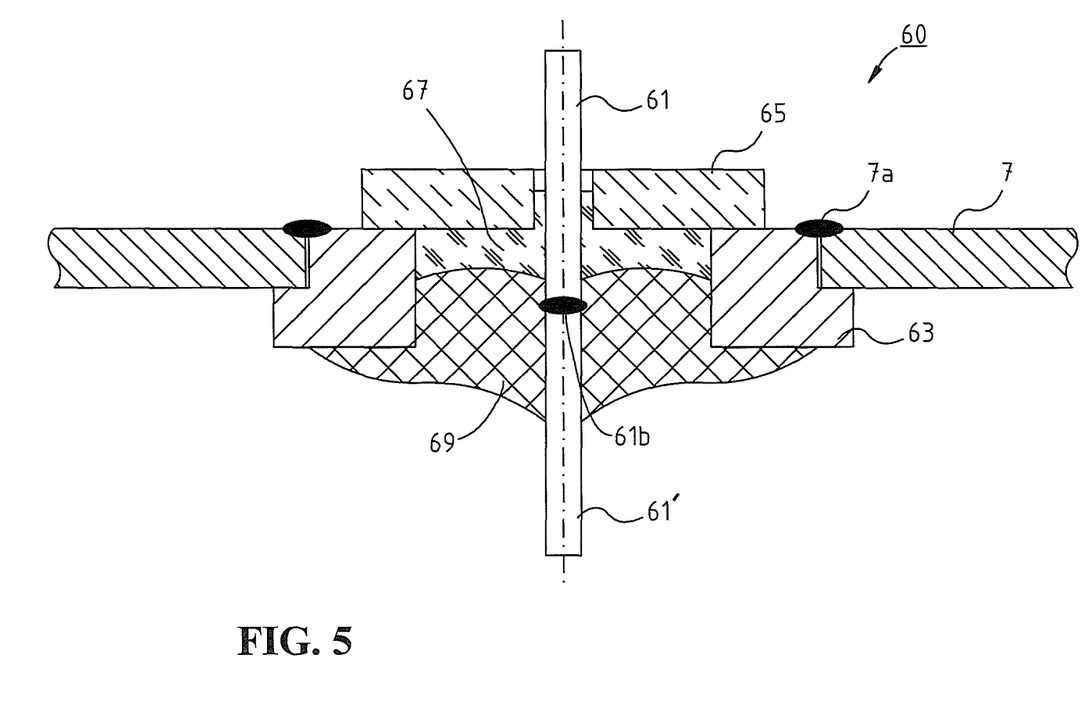

FIG. 5 shows a slight alteration of the design 60 shown in FIG. 4, in which the filler plug 69 completely fills up the hole of the flange 53 and wets a larger area of the inner terminal pin section 61'. This has the advantage that the joint 61b between the pin sections 61 and 61' does not have to be located inside the hole of the flange 63 and can therefore be formed more easily.

Moreover, the joint can also be a welded or soldered or electrically-conductive glued joint, or the pin sections may be crimped with one another (via an additional element or via an opening (hole) or a gap of one of the two pins).

Figure 6:
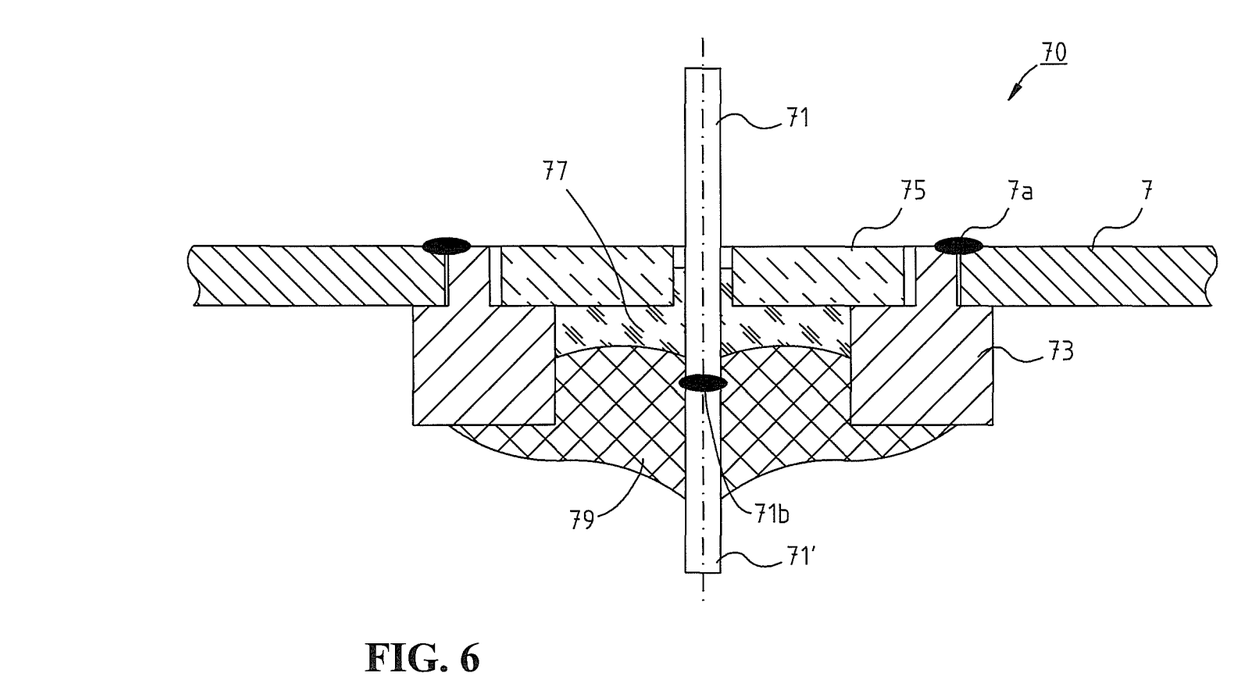

A further feedthrough 70 shown in FIG. 6 represents a slight alteration of the embodiment shown in FIG. 5, in which a widened recess is provided in the top side of the flange 73 and the ceramic disc 75 is incorporated therein in such a way that its upper front face terminates approximately flush with the upper front face of the flange 73 and, thus, an essentially flat surface of the feedthrough and the associated front face of the implant housing is provided overall (with incorporation of the upper housing section 7). In a design variant not shown here, this principle of having the embedded ceramic disc can also be transferred to a ceramic disc located on the inner side of the implant housing. The ceramic disc(s) provided with a central opening take or takes over the task of centering the pin in relation to the central flange opening during the soldering of the glass/ceramic feedthrough in the production process.

Figure 7:
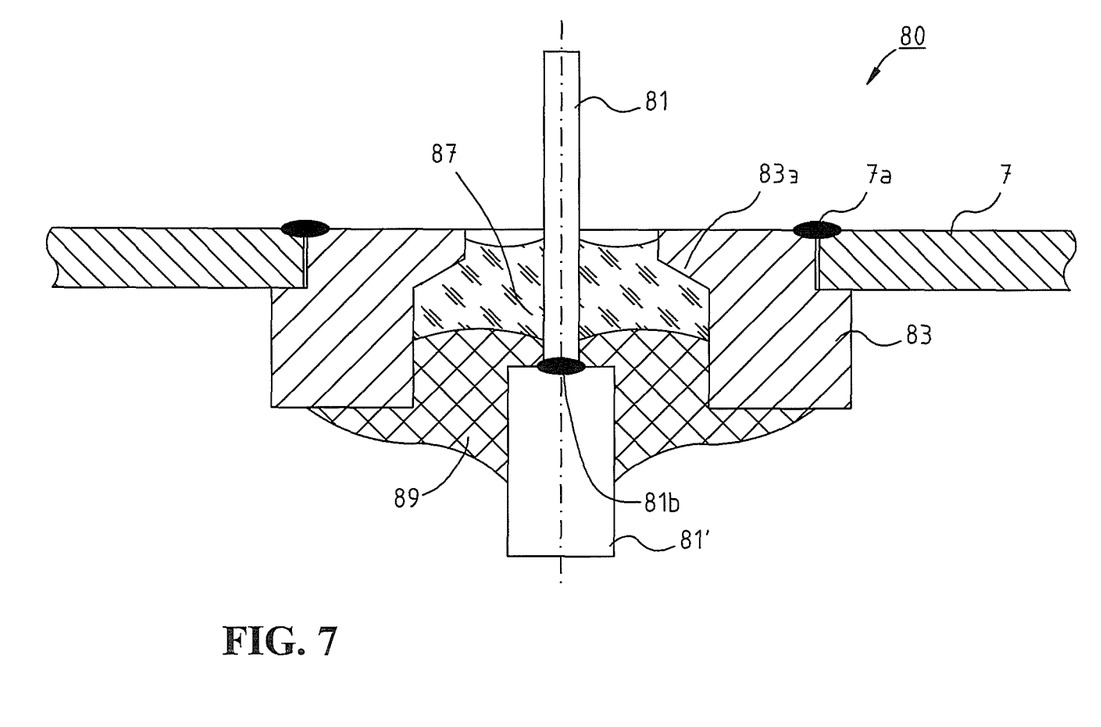

In the further feedthrough 80 shown in FIG. 7, the flange 83 has a further modified form, which allows the ceramic disc(s) provided in the other embodiments to be dispensed with. In order to ensure a favorable glass solder shape and a favorable position of the glass solder plug 87 in the flange 83, the flange 83 has a beveled section 83a pointing inward, which positions the glass solder plug during the production process and takes over the mechanical function of the ceramic disc to a certain degree in use. The inner section 81' of the terminal pin is wider (and/or thicker) here as a design variant than the outer pin section 81, in whose area the hermetically tight seal is produced via the glass solder. Moreover, the inner section may also be a plate, inter alia.

In a further design variant, the bevel section 83a can be dispensed with and the flange 83 can thus have a continuous, cylindrical opening, the position of the glass solder plug 87 in the opening of the flange 83 being established by appropriate measures during the production process, such as, for example, the use of centering units which cannot be wetted by the glass solder plug 87, such as, for example, graphite.

The embodiments of the invention are not restricted to the above-described examples and emphasized aspects, but rather are also possible in numerous alterations which are within the scope of one skilled in the art.

It will be apparent to those skilled in the art that numerous modifications and variations of the described examples and embodiments are possible in light of the above teachings of the disclosure. The disclosed examples and embodiments are presented for purposes of illustration only. Therefore, it is the intent to cover all such modifications and alternate embodiments as may come within the true scope of this invention, which is to be given the full breadth thereof. Additionally, the disclosure of a range of values is a disclosure of every numerical value within that range.

I claim:

1. A feedthrough for use in a medical electronic implant comprising:
   a terminal pin which has a first section made of a first material which can be soft soldered in the interior of the implant, and a second section made of a second material in the exterior of the implant, wherein the first and second sections are physically connected together at a joint;
   a flange enclosing the terminal pin;
   a glass solder plug which hermetically seals the terminal pin in relation to the flange; and
   a polymer filler enclosing the terminal pin and situated so that it covers the joint between the first and second sections.

2. The feedthrough according to claim 1, wherein the terminal pin, in the second section of its length in which it is in contact with the glass solder plug, has at least one core made of the second material which has approximately the same coefficient of thermal expansion as the glass solder.

3. The feedthrough according to claim 2, wherein the second material of the terminal pin or its core in the second section of its length in which it is in contact with the glass solder plug is Pt, Pt/Ir, FeNi, FeNiCo, FeCr, Nb, or Ta, or an alloy with metals of this group.

4. The feedthrough according to claim 1, wherein the second section of the terminal pin in the interior of the implant which can be soft soldered, is a nickel pin or a nickel plate.

5. The feedthrough according to claim 4, wherein the first section of the terminal pin is a niobium pin which is attached via soldering, welding, crimping or gluing in an electrically conductive manner onto the nickel pin or the nickel plate via the joint.

6. The feedthrough according to claim 4, wherein the interior nickel pin includes a nailhead.

7. The feedthrough according to claim 1, wherein the terminal pin is enclosed in the flange by a ceramic ring, wherein the glass solder plug is implemented so that it hermetically seals a ring gap between the terminal pin and the ceramic ring.

8. The feedthrough according to claim 7, wherein the ceramic ring is made of Al2O3 ceramic.

9. The feedthrough according to claim 1, wherein the polymer filler which encloses the terminal pin at the joint is provided on the interior of the glass solder plug.

10. A method for the producing a feedthrough according to claim 1, comprising the step of cooling the terminal pin using a heat sink during the generation of the glass solder plug.

11. The feedthrough according to claim 1, wherein an interior soft soldering on the first section of the terminal pin is executed using a reflow method.

12. The feedthrough according to claim 1, wherein the first section of the terminal pin has a first width that is greater than a second width of the second section of the terminal pin.

13. The feedthrough according to claim 1, wherein the flange, at an outer surface of the implant, has a beveled section pointing inward.

14. A feedthrough for use in a medical electronic implant comprising:
   a terminal pin including a first section made of a first material which can be soft soldered in the interior of the implant, and a second section made of a second material in the exterior of the implant, wherein the first and second sections are physically connected together at a joint;
   a flange enclosing the terminal pin;
   a glass solder plug which hermetically seals the second section of the terminal pin in relation to the flange; and
   a polymer filler enclosing the terminal pin and situated so that it covers the joint between the first and second sections.

15. The feedthrough according to claim 14, further comprising a ceramic ring provided adjacent the glass solder plug at an exterior of the implant, the ceramic ring enclosing the second section of the terminal pin, wherein the glass solder plug is implemented so that it hermetically seals a ring gap between the second section of the terminal pin and the ceramic ring.

16. The feedthrough according to claim 14, wherein the first material is nickel, and wherein the second material is Pt, Pt/Ir, FeNi, FeNiCo, FeCr, Nb, or Ta, or an alloy with metals of this group.

17. The feedthrough according to claim 14, wherein the first section of the terminal pin has a first width that is greater than a second width of the second section of the terminal pin.

18. The feedthrough according to claim 17, wherein the terminal pin includes a tapered section adjacent the joint, the tapered section tapering from the first width of the first section to the second width of the second section.

19. The feedthrough according to claim 14, wherein the flange, at an outer surface of the implant, has a beveled section pointing inward.

20. The feedthrough according to claim 14, wherein the first and second sections of the terminal pin are attached at the joint via soldering, welding, crimping or gluing in an electrically conductive manner.

* * * * *